United States Patent [19]

Pawlowski

[11] Patent Number: 4,464,552
[45] Date of Patent: Aug. 7, 1984

[54] PACKAGING

[75] Inventor: Thomas D. Pawlowski, Neenah, Wis.

[73] Assignee: James River-Dixie/Northern, Inc., Norwalk, Conn.

[21] Appl. No.: 316,135

[22] Filed: Oct. 29, 1981

[51] Int. Cl.³ .............................................. B65D 69/00
[52] U.S. Cl. .................................... 206/569; 206/460; 206/820; 206/804
[58] Field of Search ............... 206/820, 103, 104, 102, 206/380, 460, 569, 804

[56] References Cited

U.S. PATENT DOCUMENTS

| | | | |
|---|---|---|---|
| 2,165,539 | 7/1939 | Dahlgren | 206/460 |
| 2,247,252 | 6/1941 | Price | 206/460 |
| 3,347,361 | 10/1967 | Lindeke | 206/460 |
| 3,420,364 | 1/1969 | Kennedy, Jr. | 206/460 |
| 3,583,358 | 6/1971 | Hanson, Jr. | 206/460 |
| 4,015,708 | 4/1971 | Kelm | 206/460 |
| 4,053,049 | 10/1977 | Beauvais | 206/460 |
| 4,055,249 | 10/1977 | Kojima | 206/460 |
| 4,317,852 | 3/1982 | Ogden | 206/460 |

FOREIGN PATENT DOCUMENTS 71910   1/1916   Fed. Rep. of Germany ...... 206/380

Primary Examiner—Joseph Man-Fu Moy
Attorney, Agent, or Firm—Finnegan, Henderson, Farabow, Garrett & Dunner

[57] ABSTRACT

A dispensing package for diabetic test care strips of paper includes a paperboard pouch containing a test strip unit. The pouch has a reclosable flap affording access to the contained test strip unit, the latter comprising a paperboard backing panel having a tab on one end accessible at the opening of the pouch. Attached to the other end of the panel is the edge portion of a stack of test strip material having parallel cuts extending from the free edge of the stack toward the attached edge, and which cuts define test strips adapted to be torn from the unit after it is removed partially or entirely from the pouch.

5 Claims, 3 Drawing Figures

PACKAGING

BACKGROUND OF THE INVENTION

This invention relates to packaging, and more particularly to an improved package for dispensing diabetic care test strips.

Packaging of diabetic care test strips generally takes the form of placing the loose strips in a bottle or like container. The strips are then removable in random fashion, by hand, in the course of which the removed strip as well as the others in the bottle are subject to contamination. A container of this type while having this disadvantage, has a further disadvantage in that it is bulky for carrying in one's pocket, purse or the like, since the test strips normally are used by a person, routinely, in the course of a day's activities.

It is a general objective of this invention to provide an improved package for dispensing test strips and the like affording ease of carrying and minimal handling by the user.

SUMMARY OF THE INVENTION

In achievement of the foregoing as well as other objectives, the invention contemplates in an improved dispensing package, the combination of a pouch including an opening, a closure flap on said pouch for folding over said opening, and a diabetic care test strip unit in said pouch and removable through said opening, said unit including a paperboard backing panel having a tab presented for grasping adjacent said opening, and a stack of diabetic care test sheets attached to said backing panel in a region thereof spaced from said tab, said sheets having a plurality of cuts extending from a free edge thereof toward said region of attachment and defining a plurality of test strips in each said sheet, said test strip unit being removable from said pouch by opening said closure flap, and grasping and pulling said tab to present a test strip for removal by tearing from said unit.

The manner in which the foregoing as well as other objectives and advantages of the invention may best be achieved will be more fully understood from a consideration of the following description, taken in light of the accompanying drawing.

DESCRIPTION OF THE PREFERRED EMBODIMENT

Figure 1:
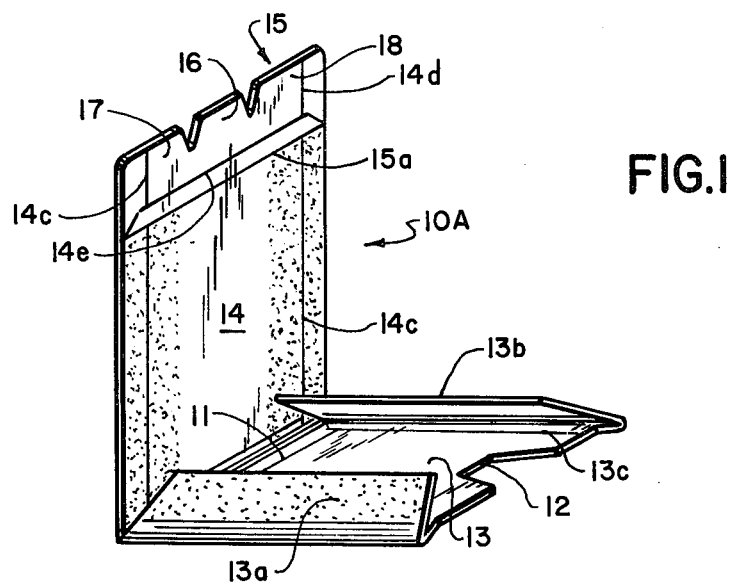
FIG. 1 is a perspective view of a partially folded paperboard blank from which the pouch is set up.

With more detailed reference to the Drawing, there is seen in FIG. 1 a partially folded, suitably cut and scored paperboard blank 10A, including front and rear wall panels 13, 14, respectively, joined along score line 11, glue flaps 13a, 13b, a notch 12 in wall panel 13, and a closure flap 15 hinged along score line 15a on rear wall panel 14. Flap 15 is provided with a locking tab 16, and a pair of opening tabs 17 and 18.

Figure 2:
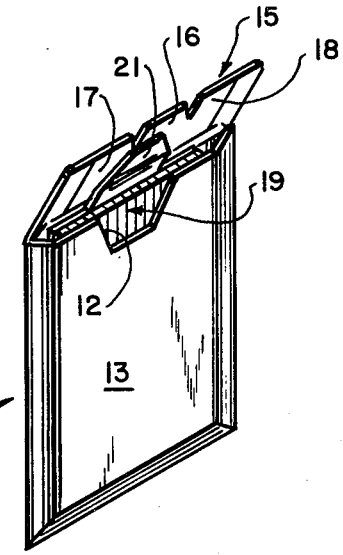
FIG. 2 is a perspective view of an opened, set-up pouch with a test strip unit in place.

With reference to FIG. 2, a rectangular pouch 10 has been set up from blank 10A by folding wall panels 13 and 14 toward one another and gluing flaps 13a, 13b to rear wall panel 14.

Figure 3:
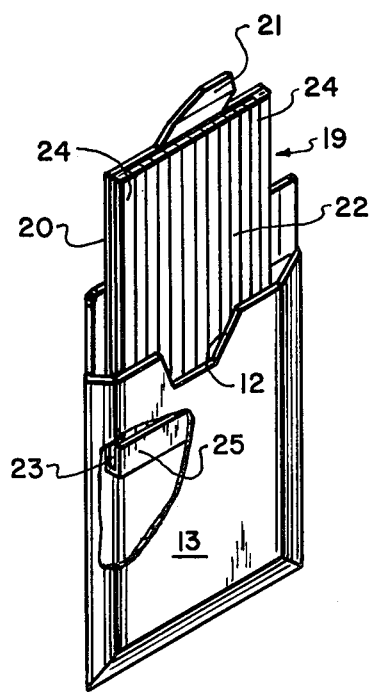
FIG. 3 is a fragmented perspective view similar to FIG. 2, with the test strip unit partially removed.

In especial accordance with the invention, and with reference also to FIG. 3, a diabetic care test strip unit 19 is slidably insertable and removable through the opening in pouch 10 defined by the non-joined ends of wall panels 13 and 14. Unit 19 comprises a rectangular backing panel 20 received within the pouch and provided with a tab 21 at its one end foldable down in registry with notch 12 in wall 13, adjacent the pouch opening. On backing panel 20 are a stack of sheets 22 of test material, such as sensitized paper, adherent to one another and to the panel 20 in a region 23 along an edge of the panel opposite the edge on which tab 21 is provided. Sheets 22 need not be adhered in region 23, and to one another. Instead, for example, the assembled stack of sheets may be stapled or otherwise suitably attached to panel 20. Each sheet 22 includes parallel knife cuts that define an orderly stack of test strips 24 in parallel array, free at the tab edge and supported in the region 23 of backing panel 20. Advantageously, the supported ends only of the strips 24 need be the sensitized region of the strip, leaving the free ends devoid of sensitization. Stated another way, each test strip 24 is sensitized substantially solely in a region intermediate its free end, i.e., the free edge of sheet 22 from which it is cut, and the region of attachment to panel 20. Further to test unit 19, the adherent edge of panel 20 is folded over the end of the stack as seen at 25, further to rigidify the unit.

Since the unit 19 has considerable thickness, each of walls 13 and 14 is provided with score lines 13c, 14c, respectively, in a generally U-shaped array spaced inwardly of the closed edges of the pouch, in provision of relief lines accommodating controlled bulging of the filled pouch. Also in accommodation of bulging, flap 15 includes a pair of score lines 14d aligned with score lines 14c, and a score line 14e having its central segment parallel to score line 15a and including curved ends intersecting score line 15a. Initial, sealing closure of the pouch and its contents is provided, although not shown, by a suitable overwrap (not shown) of known construction.

In use, the pouch is opened by releasing the overwrap, folding flap 15 from a closed position (not shown), in which locking tab 16 is behind front wall panel 13 at notch 12, to its open position shown in FIG. 2, and, while holding the pouch in one hand, grasping and pulling tab 21 to slide unit 19 partially as shown in FIG. 3, or entirely from the pouch. In either case, unit 19 is held in the region of attachment or adherence 23, for example at folded portion 25 of backing panel 20, and a strip 24 to be removed is grasped at its free end and torn from panel 20. Since unit 19 need not be removed from the pouch, contamination-free use of the test strips further is ensured. Following removal of a strip, the unit is pushed back into the pouch, tab 21 is folded over into notch 12, flap 15 is closed, and locking tab 16 is inserted into notch 12 behind front wall 13.

Alternatively as respects the relocking means for flap 15, tabs 16, 17, and 18 may be combined into a single tab and provided, along with the underlying portion of front wall 13, with a pressure sensitive coherent material of known composition. As a further alternative, a pressure sensitive tape may be applied to extend over the single tab onto front wall 13, for selective release and attachment thereto.

It will be appreciated that the invention achieves an improved package structure for test strips facilitating both use and storage of the strips. The flat package is truly pocket size and its contents are maintained free of contamination during storage and use.

While a preferred embodiment and some modifications of the invention have been described, these and other modifications may be resorted to within the scope of the appended claims.

I claim:

1. In an improved dispensing package, the combination of a pouch including an opening and a closure flap for folding over said opening, and a diabetic care test strip unit in said pouch and removable through said opening, said unit including a paperboard backing panel having a tab presented for grasping adjacent said opening, and a stack comprising at least two sheets of test material including sensitized paper, each sheet having a plurality of parallel knife cuts defining diabetic care test strips in orderly array, said sheets being attached to one another and to said backing panel in a region along an edge of said panel opposite the edge provided with said tab and having free ends in the region of said tab, said test strip unit being removable from said pouch, without handling said sensitized paper, by opening said closure flap, and grasping and pulling said tab to present the free end of a test strip for removal by tearing from said unit.

2. The dispensing package of claim 1, wherein said backing panel includes a portion folded over said stack of strips in the recited region of attachment to rigidify said unit.

3. The dispensing package of claim 1 or 2, wherein said strips of said stack are adherent to one another in the region of attachment to said backing panel.

4. The dispensing package of claim 1 or 2, wherein said test strips are sensitized substantially solely in a region intermediate said free ends and said region of attachment.

5. The dispensing package of claim 3, wherein said test strips are sensitized substantially solely in a region intermediate said free ends and said region of attachment.

* * * * *